United States Patent [19]

Hofer et al.

[11] 4,107,138

[45] Aug. 15, 1978

[54] PHOSPHONOUS AND THIOPHOSPHONOUS ACID ETHERS AS STABILIZERS FOR ORGANIC MATERIALS

[75] Inventors: Kurt Hofer, Münchenstein; Guenther Tscheulin, Riehen, both of Switzerland

[73] Assignee: Sandoz Ltd., Basle, Switzerland

[21] Appl. No.: 575,524

[22] Filed: May 8, 1975

Related U.S. Application Data

[60] Division of Ser. No. 455,597, Mar. 28, 1974, Pat. No. 3,903,208, Continuation-in-part of Ser. No. 308,594, Nov. 21, 1972, Pat. No. 3,875,264.

[30] Foreign Application Priority Data

Nov. 24, 1971 [CH] Switzerland .......................... 17129/71

[51] Int. Cl.[2] .......................... C08K 5/49; C08K 5/53

[52] U.S. Cl. .......................... 260/45.7 P; 106/177; 260/45.7 PS; 260/799; 260/865; 260/870

[58] Field of Search .......................... 260/45.7 P, 45.7 PS, 260/799; 106/177

[56] References Cited

U.S. PATENT DOCUMENTS

| | | | |
|---|---|---|---|
| 2,510,777 | 6/1950 | Gray | 260/45.7 P |
| 2,653,161 | 9/1953 | Ballard et al. | 252/46.6 |
| 2,739,123 | 3/1956 | Kennerly et al. | 252/32.7 |
| 3,331,797 | 7/1967 | Kopetz et al. | 260/45.7 RL |
| 3,493,538 | 2/1970 | Salyer et al. | 260/45.95 |
| 3,809,676 | 5/1974 | Liberti | 260/45.75 |
| 3,875,108 | 4/1975 | Koch et al. | 260/45.7 RL |
| 3,903,208 | 9/1975 | Hofer et al. | 260/951 |
| 3,953,539 | 4/1976 | Kawase et al. | 260/45.7 P |

*Primary Examiner*—Donald E. Czaja
*Assistant Examiner*—R. A. White
*Attorney, Agent, or Firm*—Gerald D. Sharkin; Richard E. Vila; Thomas C. Doyle

[57] ABSTRACT

Organic materials are stabilized against the effects of heat, light or oxygen by addition of a compound of the formula

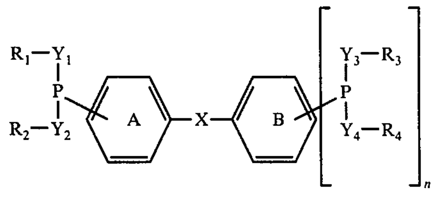

wherein X is $-CH_2-$, $-O-$ or $-S-$, $Y_1$, $Y_2$, $Y_3$ and $Y_4$ are $-O-$ or $-S-$, $R_1$, $R_2$, $R_3$ and $R_4$ are hydrogen or hydrocarbon radicals

*n* is 0 or 1 and rings A and B may be further substituted by 1 or 2 alkyl groups or an inorganic salt of such a compound in which any of $R_1$-$R_4$ are hydrogen.

12 Claims, No Drawings

PHOSPHONOUS AND THIOPHOSPHONOUS ACID ETHERS AS STABILIZERS FOR ORGANIC MATERIALS

This is a division of application Ser. No. 455,597 filed Mar. 28, 1974, now U.S. Pat. No. 3,903,208, which in turn is a continuation-in-part of application Ser. No. 308,594 filed Nov. 21, 1972, now U.S. Pat. No. 3,875,264.

The present invention relates to phosphonous acid derivatives.

More particularly, this invention provides compositions comprising an organic material which is susceptible to degradation by light, oxygen or heat and an amount effective to stabilize said material against said degradation of a compound of formula I,

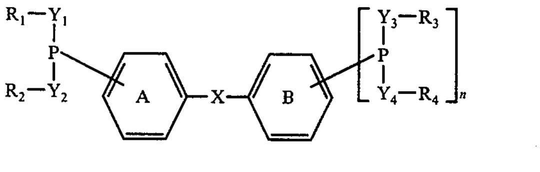

I in which

*n* is 0 or 1,

X is $-CH_2-$, $-O-$, or $-S-$, $Y_1$, $Y_2$ $Y_3$ and $Y_4$, which may be the the same or different, each is $-O-$ or $-S-$, $R_1$, $R_2$, $R_3$ and $R_4$, which may be the the same or different, each is hydrogen or a hydrocarbon radical of up to 20 carbon atoms consisting of aromatic and/or saturated aliphatic and/or cycloalkyl units, and rings A and B may be either further unsubstituted or each further substituted by 1 or 2 alkyl groups of 1 to 6 carbon atoms, and salts of compounds in which any of $R_1$ to to $R_4$ is hydrogen with an inorganic cation.

X preferably signifies -O- and n preferably signifies 1. $Y_1$, $Y_2$, $Y_3$ and $Y_4$ are preferably the same, and $R_1$, $R_2$, $R_3$ and $R_4$ are preferably also the same. In the preferred compounds, the >P- substituent or each >P- substituent is in the para position of the nucleus.

Suitable hydrocarbon radicals for $R_1$, $R_2$, $R_3$ and $R_4$ include the following:- alkyl radicals, preferably other than tertiary alkyl radicals, of up to 20, preferably up to 12, in particular 1 to 6 carbon atoms, for example n-alkyl radicals such as methyl, ethyl, propyl, butyl, pentyl, hexyl, heptyl, octyl, nonyl, decyl, undecycl and dodecyl, secondary alkyl radicals such as isopropyl, 2-butyl, 3-methyl-2-butyl, 2-pentyl, 2,2-dimethyl-3-butyl, 2-hexyl, 3-hexyl, 2-methyl-3-phenyl, 3-methyl-2-pentyl, 4-methyl-2-pentyl, 2,2-dimethyl-3-pentyl, 2,4-dimethyl-3-pentyl, 2-heptyl, 3-heptyl, 4-heptyl, 2-methyl-3-hexyl, 4-methyl-3-hexyl, 5-methyl-3-hexyl, 3-ethyl-4-hexyl, 2,2-dimethyl-3-hexyl, 2,4-dimethyl-3-hexyl, 2,5-dimethyl-3-hexyl, 3,4-dimethyl-2-hexyl, 2-methyl-3-heptyl, 3-methyl-2-heptyl, 3-methyl-4-heptyl, 4-methyl-3-heptyl, 5-methyl-3-heptyl, 6-methyl-2-heptyl, 2-octyl, 3-octyl, 4-octyl, 2,2,4-trimethyl-3-pentyl, 5-ethyl-2-heptyl, 2,2-dimethyl-3-heptyl, 2,6-dimethyl-4-heptyl, 2-methyl-3-octyl, 3-methyl-4-octyl, 6-ethyl-3-octyl, 2-decyl, 5-decyl, 2,2-dimethyl-3-octyl, 2-methyl-4-nonyl, 3-methyl-4-nonyl, 6-ethyl-3-decyl, 7-ethyl-2-methyl-4-nonyl, 2-dodecyl, 2,6,8-trimethyl-4-nonyl, 2-tridecyl, 2-tetradecyl, 2-pentadecyl, 2-hexadecyl, 2-nonadecyl, alkyl radicals bounds through a primary carbon atom but otherwise branched, for example 2-methyl-1-propyl, 2,2-dimethyl-1-propyl, 2-methyl-1-butyl, 2-ethyl-1-butyl, 2,2-dimethyl-1-butyl, 2-methyl-1-pentyl, 3-methyl-1-pentyl, 4-methyl-1-pentyl, 2,4-dimethyl-1-pentyl, 2-ethyl-1-hexyl, 2,2-dimethyl-1-hexyl, 2,2,4-trimethyl-1-pentyl, 4-methyl-2-propyl-1-pentyl, 3,7-dimethyl-1-octyl, 2,2-dimethyl-1-decyl; cycloalkyl radicals of up to 20, preferably 3 to 12, in particular 5 to 8 carbon atoms, optionally substituted by 1, 2 or 3 alkyl radicals, for example of 1 to 4 carbon atoms, such as cyclopentyl, cyclohexyl, cycloheptyl, 2-, 3- or 4-methyl-cyclohexyl, cyclooctyl, 2,5-, 2,6-, 3,4- or 3,5-dimethylcyclohexyl, 2-propylcyclohexyl, 3,3,5-trimethylcyclohexyl, 2-butylcyclohexyl, 4-tert.butylcyclohexyl, 3-methyl-6-isopropylcyclohexyl, cyclododecyl, 1-methylcyclopentyl, 1-methylcyclohexyl, 1-methylcycloheptyl, 1-propylcyclopentyl, 1-butylcyclopentyl, 1-butylcyclohexyl and 1-pentylcyclopentyl; cycloalkylalkyl radicals, in particular $C_{5-8}$ cycloalkyl $C_{1-6}$ alkyl radicals, for example cyclohexyl-methyl, 2-cyclohexyl-ethyl, cycloheptylmethyl 1-cyclohexylpropyl, 3-cyclohexylpropyl, cyclooctylmethyl, cycloundecylmethyl and cyclododecylmethyl; aryl radicals, for example phenyl or diphenyl, optionally substituted by 1, 2 or 3 alkyl radicals, e.g. of 1 to 12, preferably 1 to 6 carbon atoms, such as those alkyl radicals mentioned above and also tertiary alkyl radicals, such as tert. butyl, 2-methyl-2-butyl, 2,3-dimethyl-2-butyl, 2-methyl-2-pentyl, 3-methyl-3-pentyl, 3-ethyl-3-pentyl, 2,4-dimethyl-2-pentyl, 2-methyl-2-hexyl, 3-methyl-3-hexyl, 3,4-dimethyl-3-hexyl, 3,5-dimethyl-3-hexyl, 2-methyl-2-heptyl, 3-methyl-3-heptyl, 4-methyl-4-heptyl, 2,3,4-trimethyl-3-pentyl, 2,4,4-trimethyl-2-pentyl, 3-ethyl-3-heptyl, 2-methyl-2-octyl, 4-methyl-4-octyl, 3,6-dimethyl-3-octyl, 3,7-dimethyl-3-octyl, 2,4,4,6,6-pentamethyl-2-heptyl, as well as 1-alkyl substituted cycloalkyl radicals, such as those mentioned above; examples of such substituted aryl radicals include 2-, 3- and 4-methylphenyl, 2,3-, 2,4-, 2,5-, 3,4- and 3,5-dimethylphenyl, 2-, 3- and 4-ethylphenyl, 2,3,5- and 2,4,5-trimethylphenyl, 3-ethyl-5-methylphenyl, 4-sec.-butyl-phenyl, 2- and -4- tert.butylphenyl, 5-isopropyl-2-methylphenyl, 2-isopropyl-5-methylphenyl, 3-isopropyl-5-methylphenyl, 4-tert.pentylphenyl, 2-tert.butyl-4-methylphenyl, 4-tert.butyl-2-methylphenyl, 6-tert.butyl-3-methylphenyl, 2,4-di-tert.butylphenyl, 4-(1',1',3',3'-tetramethylbutyl)-phenyl, 2-methyl-4-(1',1',3",3'-tetramethylbutyl)-phenyl, 4-nonylphenyl (mixture of isomers), and 2,4-di-tert.octyl-phenyl; aralkyl radicals, such as phenyl or diphenyl alkyl radicals, the alkyl radicals of which suitably contain 1 to 12, particularly 1 to 6 carbon atoms, and the aryl radicals of which may optionally be alkyl substituted as above, including benzyl, 1- and 2-phenyl-ethyl, 1-phenyl-1-propyl, 1-phenyl-2-propyl, 2-phenyl-1-propyl, 3-phenyl-1-propyl, 1-(o-tolyl)-ethyl, 1-(m-tolyl)-ethyl, 1-(p-tolyl)-ethyl, 1-phenyl-1-butyl, 2-(2',4',6'-trimethyl-phenyl)-ethyl, 1-phenyl-1-pentyl, 1-(4'-tert.butylphenyl)-ethyl, 4-methyl-1-phenyl-2-pentyl and benzohydryl. The preferred hydrocarbon radicals for $R_1$, $R_2$, $R_3$ and $R_4$ include alkyl radicals, other than tertiary alkyl radicals, of 1 to 12, in particular 4 to 12 carbon atoms, such as n-butyl or n-dodecyl, and phenyl and diphenyl radicals, optionally substituted by 1 or 2 alkyl radicals of 1 to 4 carbon atoms, preferably tertiary such alkyl radicals, such as 2,4-di-t-butylphenyl, 2-t-butyl-diphenyl, and 2,4'-di-t-butyldiphenyl.

The rings A and B may, as indicated, be substituted by 1 or 2 alkyl groups of up to 6, preferably up to 4 carbon atoms, for example such alkyl groups as mentioned above, but are preferably unsubstituted.

The invention also provides a process for the production of compounds of formula I and inorganic salts thereof, characterised by reacting a compound of formula II,

II

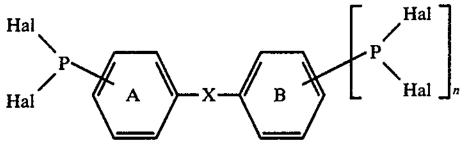

in which

X, *n* and rings A and B are as defined above, and the radicals Hal, which may be the same or different, each signify a halogen atom, with compounds of formula III and IV,

| | |
|---|---|
| $HY_1R_1$<br>III | $HY_2R_2$<br>IV |

in which $R_1$, $R_2$, $Y_1$ and $Y_2$ are as defined above, and, if n signifies 1, with compounds of formula V and VI,

| | |
|---|---|
| $HY_3R_3$<br>V | $HY_4R_4$<br>VI |

in which $R_3$, $R_4$, $Y_3$ and $Y_4$ are as defined above, and, where required, converting the resulting product into an inorganic salt. As will be appreciated, two or more of the compounds III, IV, V and VI may be the same, in which case the molar quantity of the compound is adjusted accordingly.

The process of the invention may suitably be carried out in conventional manner, for example as described by K. Sasse, Houben-Weyl (eds.), Methoden der organischen Chemie, 4th impression (1963), Vol. XII/1, pp. 318/ff. As will also be appreciated, however, the particular conditions employed depend, to an extent, on the particular compounds III, IV, V or VI being employed. For example, in some instances, it may be advisable to apply external cooling to the reaction mixture to restrain the vigorous reaction. Thus, for example, when any of the compounds III, IV, V and VI is water, then it is preferable to employ in the reaction mixture an excess of water and to add the compound II with cooling and stirring and at a rate slow enough to ensure that the exothermic reaction does not lead to an unduly high temperature. Where the compounds III, IV, V or VI are alcohols or phenols, the reaction may suitable be carried out at a temperature of from 100° to 150° C, in the presence of an acid binding agent such as pyridine or a trialkylamine.

Where the compound II is reacted with water, products are formed containing radicals of formula VII*a* and VII *b*,

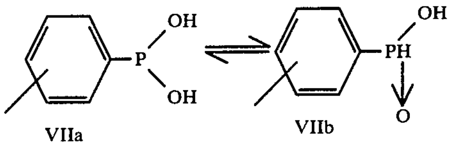

VIIa VIIb which are acidic and may be converted into salts with inorganic cations.

Conversion of the acidic compounds into the salts may be effected in conventional manner. Suitable salts include alkali metal, e.g. sodium or potassium, alkaline earth metal, e.g. calcium or magnesium, zinc, manganese, aluminium, copper, vanadium, cobalt and nickel salts. The salts may be produced by reaction of the free acid with a metal hydroxide or salt, such as calcium hydroxide, zinc oxide, sodium carbonate, potassium bicarbonate, aluminium acetate, barium chloride, nickel acetate and zinc chloride.

Preferably, however, the reaction of the compounds II with water and production of salts is carried out in a single operation. For this purpose, an excess of water may be provided for hydrolysis of the compound II, and after addition of the appropriate inorganic reagent, the compound II may be slowly added, with stirring, as indicated above.

The resulting compounds of formula I and with inorganic cations salts thereof may be isolated and purified using conventional techniques.

The compounds of formula II, employed as starting materials are either known or may be produced in conventional manner from available materials, for example as described by K. Sasse, Houben-Wehl (eds.), Methoden der organischen Chemie, 4th impression (1963), Vol. XII/1, organische Phosphorverbindungen, Part 1, pp. 302-318. Thus, for example, the compound IIa, IIa

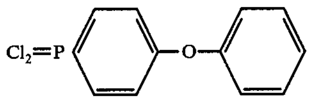

is described in Journal of the Chemical Society, 1932, 2880. In general, compounds of formula II may be produced by reacting the appropriate diphenylmethane, oxide or sulphide, with a phosphorus trihalide, preferably phosphorus trichloride. The process may suitably be effected at an elevated temperature in the gaseous phase, although it is more preferable to react under milder conditions in the presence of a catalyst, e.g. a Friedel-Krafts catalyst, in particular aluminium trichloride. It is preferable to work with phosphorus trichloride at its boiling temperature. After reaction, any aluminium chloride complex of the compound II may be decomposed, for example with phosphorus oxychloride or pyridine.

The resulting compounds of formula II may be isolated and purified using conventional techniques.

The compounds of the invention are useful as stabilizers for organic materials which are sensitive to light, oxygen and heat. For this purpose, they may be incorporated in or applied to form a protective surface film on the organic material. When thus applied, the new compounds by their stabilizing action protect sensitive materials against degradation. They have a wide area of use in the processing of plastics materials, being suitable, for example, as stabilizers for cellulose acetate, cellulose acetobutyrate, polyethylene, polypropylene, polyvinyl chloride, polyvinyl chloride acetate, polyamides, polystyrene, ethyl cellulose, cellulose nitrate, polyvinyl alcohol, silicon rubber, cellulose propionate, melamine-formaldehyde resins, urea-formaldehyde resins, allyl casting resins, polymethyl methacrylate, polyesters, polyacrylonitrile, and copolymers of these polymers. The compounds may also be used for the stabilization of natural products such as rubber, cellulose, wool and silk.

The materials for stabilization may suitably be in the form of films, sheets, rods, coatings, panels, tapes, fibres, granules, powders or other processing forms, or as solutions, emulsions or dispersions. The stabilizing compounds may be incorporated in or coated on the materials by conventional methods. An important method of application consists in intimately mixing polymeric material, for example polypropylene granules, with the stabilizer in a kneader or other suitable machine, followed by extrusion. This method ensures homogeneous distribution which is important for good protection. The material can be extruded, for example, as film, tubing or filament, the latter for conversion into textiles. In this method of application, the stabilizer may be incorporated in, for example, the polypropylene prior to textile production. The new stabilizers, however, can also be applied to textile yarns and fabrics from an aqueous medium containing a finely dispersed compound of formula (I). This method is particularly suitable for, e.g. textiles of polyethylene terephthalate and cellulose acetate fibres.

Synthetic polymeric materials need not necessarily be in the final form before incorporation of the compounds of the invention. Thus, these compounds may be mixed with the monomers or prepolymers prior to the condensation or other polymerization reaction giving the final polymer.

The new stabilizers are suitable for application to, for example, clear films and plastics, and are also suitable for stabilizing opaque, semi-opaque and translucent materials having a surface susceptible to degradation by ultra-violet radiation, air or heat. Examples of such materials are foam plastics, opaque films and coatings, opaque papers, opaque and transparent pigmented plastics, fluorescent pigments, automobile and furniture polishes, creams, lotions and related products, which may be opaque, clear or translucent.

As regards the constitution of compounds of formula I and their action, it may be mentioned that particularly good stabilization is obtained in polyalkylenes, notably polypropylene, when the molecule of the compound of the invention consists to a large extent of saturated aliphatic groups. When phosphonous acids of formula I in which $R_1$, $R_2$, $R_3$ and $R_4$ represent hydrogen are employed in the form of the nickel salts, the stabilizing action against visible light and ultra-violet radiation is particularly effective, especially in polyalkylenes. The manganese and copper salts are particularly suitable for stabilizing polyamides against degradation by ultra-violet radiation, while the salts of other transition metals such as vanadium and cobalt, are suitable as ultra-violet absorbers in a number of substrates.

The present invention also comprises the sensitive organic materials containing a compound of formula I for stabilization. As previously indicated, the new compounds can be incorporated in the organic materials at any stage of processing using standard methods. The amounts of stabilizer employed may vary within wide limits, for example from 0.01 to 5% or preferably from 0.05 to 1% in relation to the weight of the material. The stabilized organic materials may contain compounds of formula I alone, or together with further additives, for example ultra-violet absorbers and other stabilizers against degradation by heat and oxygen. As regards the latter, suitable stabilizers are those belonging to different chemical classes to the compounds of formula I, for example organic compounds of sulphur, tin and pentavalent phosphorus, sterically hindered phenols, 2-hydroxy-benzophenones and hydroxybenzotriazoles. Often, notably high stabilization may be obtained with such mixtures since they may have a synergistic action.

In the following Examples the parts and percentage are by weight and the temperatures in degrees centigrade.

EXAMPLE A

Production of an Intermediate of Formula II

A solution of 51.3 parts of diphenyl ether, 165 parts of phosphorus trichloride and 106 parts of $AlCl_3$ is heated for 3 hours, at reflux, in the absence of moisture. 122.6 parts of phosphorus oxychloride are added and stirring is continued for 15 minutes. After cooling to 0°, the $AlCl_3$-$POCl_3$ complex, which settles out in granular form, is filtered, washed thoroughly with chlorobenzene, and the filtrate evaporated under vacuum. The 4,4'-diphenylether-(bis-dichlorophosphine) of formula II*c*,

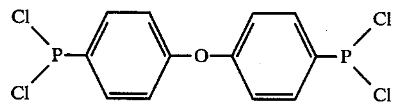

IIc is obtained in the form of a pale red oil with a pungent odour.

EXAMPLE 1

In the absence of moisture, a solution of 20 parts of the diphenylether dichlorophosphine of formula II*a*, above, in 50 parts of toluene is added at 0°-5° to 29.9 parts of dodecyl mercaptan and 15 parts of triethylamine in 100 parts of toluene. The solution is allowed to react overnight at 40°. Subsequently, the precipitated salt is filtered, the filtrate evaporated under vacuum, and the residue crystallized from absolute ether. m.p. 25°-26°

| Elementary analysis | | C | H | P |
|---|---|---|---|---|
| $C_{36}H_{59}OPS_2$ | found | 71.4 | 9.9 | 5.6 |
| | calculated | 71.6 | 9.8 | 5.2 |

EXAMPLE 2

At 0°-5°, a solution of 33.4 parts of the diphenylether dichloro-phosphine of formula II*a*, above, in 50 parts of toluene is added to 50.7 parts of 2,4-ditert.butylphenol and 25 parts of triethylamine in 200 parts of toluene in the absence of moisture. The solution is allowed to react overnight at 40°, the precipitated product filtered, the filtrate evaporated under vacuum, and the residue crystallized from ether/methanol. m.p. 88°-89°.

| Elementary analysis | | P |
|---|---|---|
| $C_{40}H_{51}O_3P$ | found | 5.4 |
| | calculated | 5.1 |

EXAMPLE 3

A solution of 95.5 parts of 4,4'-diphenylether(bis-dichloro-phosphine of formula IIc, above, in 50 parts of toluene is added, at 0°-5°, in the absence of moisture, to 211 parts of 2,4-di-tert.butylphenol and 104 parts of triethylamine in 300 parts of toluene. The solution is allowed to react overnight at 40°, the precipitated product filtered, the filtrate evaporated under vacuum, and the residue triturated with methanol and crystallized from benzene. m.p. 77°-80°.

| Elementary analysis | | C | H | P |
|---|---|---|---|---|
| $C_{68}H_{92}O_5P_2$ | found | 77.2 | 8.4 | 5.6 |
| | calculated | 77.6 | 8.8 | 5.9 |

EXAMPLE 4

A solution of 48 parts of 4,4'-diphenylether(bis-dichlorophosphine) in 50 parts of toluene is added, at 0°-5°, in the absence of moisture, to 116.2 parts of 2-tert-.butyl-4-phenyl phenol and 52 parts of triethylamine in 300 parts of toluene. The solution is allowed to react overnight at 40°, the precipitated salt filtered, the filtrate evaporated under vacuum, and the residue triturated to a white powder, m.p. 70°-74°.

EXAMPLE 5

A solution of 45 parts of 4,4'-diphenylether(bis-chlorophosphine) in 50 parts of toluene is added, at 0°-5°, to 136.3 parts of 2,4'-di-tert.butyl-4-phenyl phenol and 49 parts of triethylamine in 300 parts of toluene, in the absence of moisture. The solution is allowed to react overnight at 40°, the precipitated salt filtered, the filtrate evaporated under vacuum, and the residue triturated to a white powder. m.p. 82°-85°.

EXAMPLE 6

A solution of 12.5 parts of 4,4'-diphenylether(bis-dichlorophosphine) in 50 parts of toluene is added at 0°-5° to 9.9 parts of butanol and 14 parts of triethylamine in 150 parts of toluene in the absence of moisture. The solution is allowed to react overnight at 40°, the precipitated salt filtered and the filtrate evaporated under vacuum to yield a pale yellow oil.

The structural formulae of the compounds produced in Examples 1 to 6 are shown in Table 1 below.

Table 1

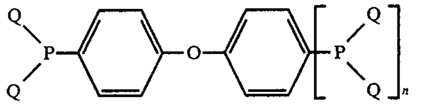

| Example No. | Significance of Q | n |
|---|---|---|
| 1 | $C_{12}H_{25}S-$ | 0 |
| 2 | 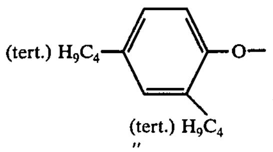 | 0 |
| 3 | " | 1 |

Table 1-continued

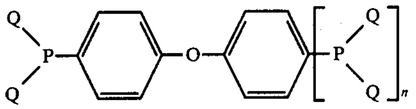

| Example No. | Significance of Q | n |
|---|---|---|
| 4 | 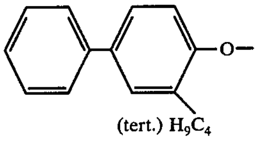 | 1 |
| 5 | 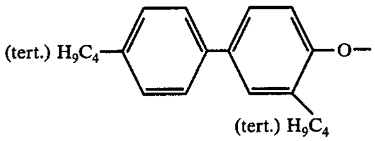 | 1 |
| 6 | $H_9C_4-O-$ | 1 |

In analogous manner to that described in Example 1, the compound of the formula:

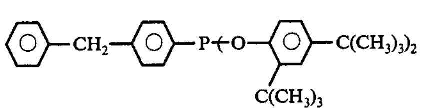

is produced.

USE EXAMPLE

A. Stabilization against Heat Discolouration

When working with polypropylene incorporating 0.2% of the stabilizer 2,2'-Methylene-bis-(4-methyl-6-tert.butylphenol) at a temperature of about 220°, a brownish colouration occurs. This can be minimised by incorporation into the polypropylene of 0.1% of a compound according to any one of Examples 1 to 6.

B. Stabilization against Oxidative Degradation

Polypropylene, which contains, as antioxidant, 0.2% of 4,4'-Methylene-bis-(2,6-di-tert.butylphenol) is intimately mixed with 0.1% of a compound produced in any one of Examples 1 to 6. The plastic is stored, in the form of thin discs, under oxygen in a closed system after removal of air. The system is then warmed to 190°, whereby an excess pressure of about 20 mm.Hg arises. The oxidation of the plastic is followed by fall in pressure. The speed of the fall in pressure is low if the activity of the stabilizer or stabiliser mixture is high. Significantly improved results are obtained with polypropylene which contains in addition to 4,4'-methylene-bis-(2,6-di-tert.butylphenol), a compound according to any one of Examples 1 to 6.

What is claimed is:

1. A composition comprising an organic material which is susceptible to degradation by light, oxygen and/or heat and an amount effective to stabilize said material against said degradation of a compound of formula I

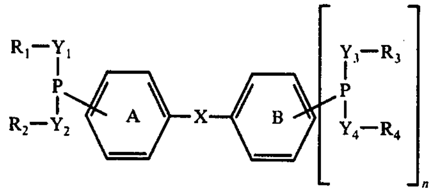

I in which $n$ is 0 or 1,

X is $-CH_2-$, $-O-$, or $-S-$, $Y_1$, $Y_2$, $Y_3$ and $Y_4$, which may be the same or different, each is $-O-$, or $-S-$, $R_1$, $R_2$, $R_3$ and $R_4$, which may be the same or different, each is hydrogen or a hydrocarbon radical of up to 20 carbon atoms consisting of aromatic and/or saturated aliphatic and/or cycloalkyl units, and rings A and B may be either further unsubstituted or each further substituted by 1 or 2 alkyl groups of 1 to 6 carbon atoms with the proviso that when $Y_1$ and $Y_2$ are oxygen and n is zero X is oxygen or sulfur.

2. A composition according to claim 1 wherein X is oxygen or sulfur when n is zero.

3. A composition according to claim 1 wherein n is 1.

4. A composition according to claim 1 wherein $Y_1$ and $Y_2$ are sulfur and $n$ is zero.

5. A composition according to claim 2 wherein the compound of formula I is present in an amount which is 0.01 to 5% by weight of the organic material.

6. A composition according to claim 5 wherein the compound of formula I is present in an amount which is 0.05 to 1% of the weight of the organic material.

7. A composition according to claim 2 wherein the organic material is selected from the group consisting of cellulose acetate, cellulose acetobutyrate, polyethylene, polypropylene, polyvinyl chloride, polyvinyl chloride acetate, polyamides, polystyrene, ethyl cellulose, cellulose nitrate, polyvinyl alcohol, cellulose propionate, melamine-formaldehyde resins, urea-formaldehyde resins, allyl casting resins, polymethyl methacrylate, polyesters, polyacrylonitrile, natural rubber and natural cellulose.

8. A composition according to claim 7 wherein the organic material is polypropylene.

9. A composition according to claim 7 wherein the compound of formula I is present in an amount which is 0.01 to 5% of the weight of the organic material.

10. A composition according to claim 9 wherein, in the compound of formula I, $R_1$, $R_2$, $R_3$ and $R_4$ are selected from the group consisting of alkyl; cycloalkyl which may be substituted by up to 3 alkyl groups; cycloalkylalkyl; phenyl which may be substituted by up to 3 alkyl or alkylcycloalkyl groups; diphenyl which may be substituted by up to 3 alkyl or alkylcycloalkyl groups; and phenyl and diphenylalkyl, the aryl portions of which may be substituted by up to 3 alkyl groups.

11. A composition according to claim 9 wherein, in the compound of formula I, $n$ is 0.

12. A composition according to claim 10 wherein the compound of formula I is of the formula

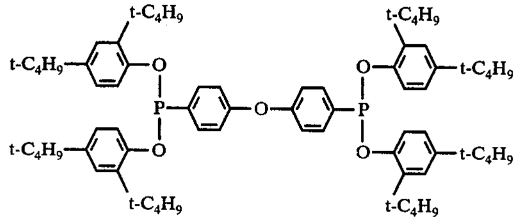

* * * * *